United States Patent
Hyon et al.

(10) Patent No.: US 7,323,211 B2
(45) Date of Patent: Jan. 29, 2008

(54) BONE-ADHERENT IMPLANT WITH SHOCK-ABSORBING PROPERTY AND MANUFACTURING METHOD THEREOF

(75) Inventors: Suong-Hyu Hyon, Kyoto (JP); Kazuaki Matsumura, Kyoto (JP); Sadami Tsutsumi, Kyoto (JP)

(73) Assignee: BMG Incorporated, Kyoto (JP)

( * ) Notice: Subject to any disclaimer, the term of this patent is extended or adjusted under 35 U.S.C. 154(b) by 0 days.

(21) Appl. No.: 10/844,734

(22) Filed: May 13, 2004

(65) Prior Publication Data

US 2004/0236432 A1   Nov. 25, 2004

(30) Foreign Application Priority Data

May 13, 2003   (JP)   .............................. 2003-171408

(51) Int. Cl.
  *B05D 1/36* (2006.01)
(52) U.S. Cl. ...................................... 427/2.26; 427/409
(58) Field of Classification Search ....... 427/2.26–2.27
  See application file for complete search history.

(56) References Cited

U.S. PATENT DOCUMENTS

| | | | | |
|---|---|---|---|---|
| 5,174,755 A | * | 12/1992 | Fukuda | ........................ 433/173 |
| 6,387,414 B1 | * | 5/2002 | Akashi et al. | .............. 424/602 |
| 6,875,461 B2 | * | 4/2005 | Tanaka et al. | ............... 427/2.1 |
| 2002/0018796 A1 | * | 2/2002 | Sewing et al. | .............. 424/423 |
| 2004/0121451 A1 | * | 6/2004 | Moritz et al. | ............ 435/287.2 |
| 2004/0161444 A1 | * | 8/2004 | Song et al. | .................. 424/423 |
| 2005/0074602 A1 | * | 4/2005 | Bjursten et al. | ............ 428/334 |

FOREIGN PATENT DOCUMENTS

JP   7-313529   12/1995

OTHER PUBLICATIONS

Tsutsumi et al, Polymer 44, pp. 6297-6301, 2003.*
Matsumura et al, Shika Zairyo, Kikai 19(4), pp. 361-366, 2000.*
Matsumura et al, J. Biomed. Mater. Res., 60, pp. 309-315, 2002.*

* cited by examiner

*Primary Examiner*—Erma Cameron
(74) *Attorney, Agent, or Firm*—Jordan and Hamburg LLP

(57) ABSTRACT

It is to provide an implant with shock-absorbing property that is able to be strongly secured in a living body as well as a manufacturing method of such implant.

The implant comprising: a substrate; a first film on the substrate, which is comprised of a polymer and has a functional group that enables adsorption of calcium ions; and a second film formed on the first film and being comprised of calcium phosphate. The manufacturing method of the implant comprising: forming said first film on a substrate; and subsequently, dipping the substrate in a calcium ion solution and in a phosphate ion solution alternately as to form the second film.

7 Claims, 3 Drawing Sheets

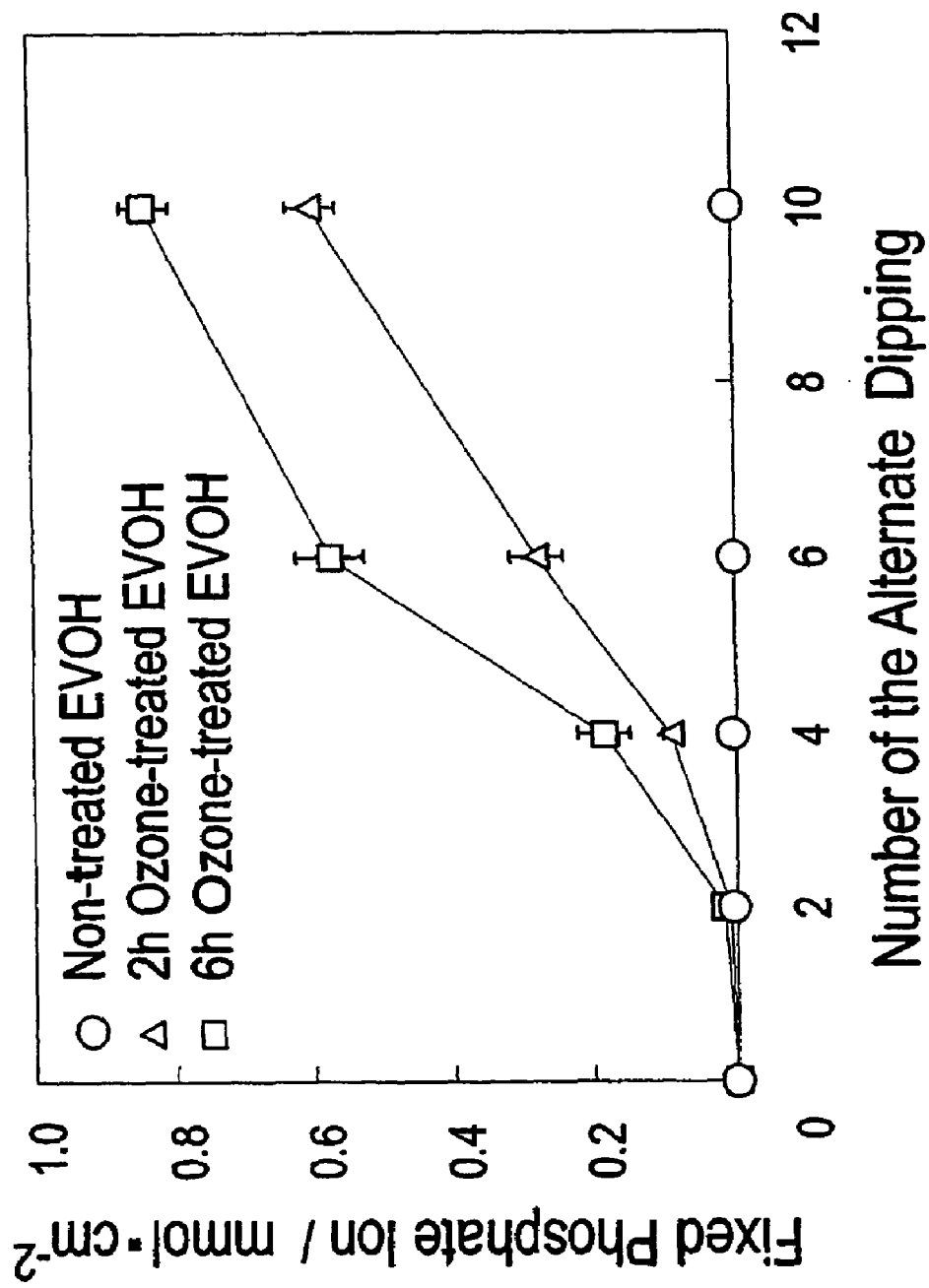

BONE-ADHERENT IMPLANT WITH SHOCK-ABSORBING PROPERTY AND MANUFACTURING METHOD THEREOF

TECHNICAL FIELD

This invention relates to Bone-adherent implants such as artificial tooth roots, artificial bones and artificial joints, and to a manufacturing method of such implants.

BACKGROUND ART

Conventionally, fractures or damages on tooth roots or bones, when occurred, are cured by implanting the implants such as artificial tooth roots or artificial bones.

For conventional tooth roots, there have been known ones formed of titanium metal and shaped as screws as to be physically secured onto jawbones. Please see, for example, JP-07(1995)-313529A (Japanese Unexamined Patent Publication H7-313529). Ones modified as follows from the above have been also known, a hydroxyapatite layer is formed on the titanium metal by a plasma vapor deposition technique, where the hydroxyapatite layer is highly compatible with the bones and facilitates conglutination with the jawbones. Please see, for example, Biomaterials 23(2002) 2569-2575, and Journal of Materials Processing Technology 65(1997) 73-79.

Whereas a natural tooth has a periodontal membrane that acts as a shock absorber, the artificial tooth of the conventional technique does not have such shock-absorbing element. Thus, dental articulation pressure is directly transmitted onto the jawbone as to hamper mechanical balance with other teeth. This may eventually cause bone resorption and thereby flailing or moving of the artificial tooth root and thus might cause serious conditions of sickness and injury by bacterial infection or the like.

Moreover, the conventional ones having a hydroxyapatite layer have a low crystallinity in respect of the hydroxyapatite and have low adhesion strength at interface with the titanium metal. Thus, dissolving away or detachment of the layer might occur so that the artificial tooth root would not be secured on the jawbone.

Hence, it is to provide an implant that is able to be strongly secured in a living body as well as a manufacturing method of such implant.

BRIEF SUMMARY OF THE INVENTION

The implant according to the invention comprises: a substrate; a film on the substrate, which is comprised of a polymer and has a functional group that enables adsorption of calcium ions; and a layer formed on the film and being comprised of calcium phosphate.

The implant according to the invention has a film comprised of a polymer, which is supposed to have a viscoelasticity, and thus has a shock-absorbing property. In view of the functional group of the film as well as the phosphate calcium that comprises the layer and highly compatible with the bone, the implant of the invention is prevented from dissolving away or detaching from the surface layers and is firmly secured on a bone in a living body.

BRIEF DESCRIPTION OF THE DRAWING

FIG. 3 is a graph showing relationship between the number of the dipping and the adsorption of phosphate ion.

DETAILED DESCRIPTION OF THE INVENTION

Figure 1:
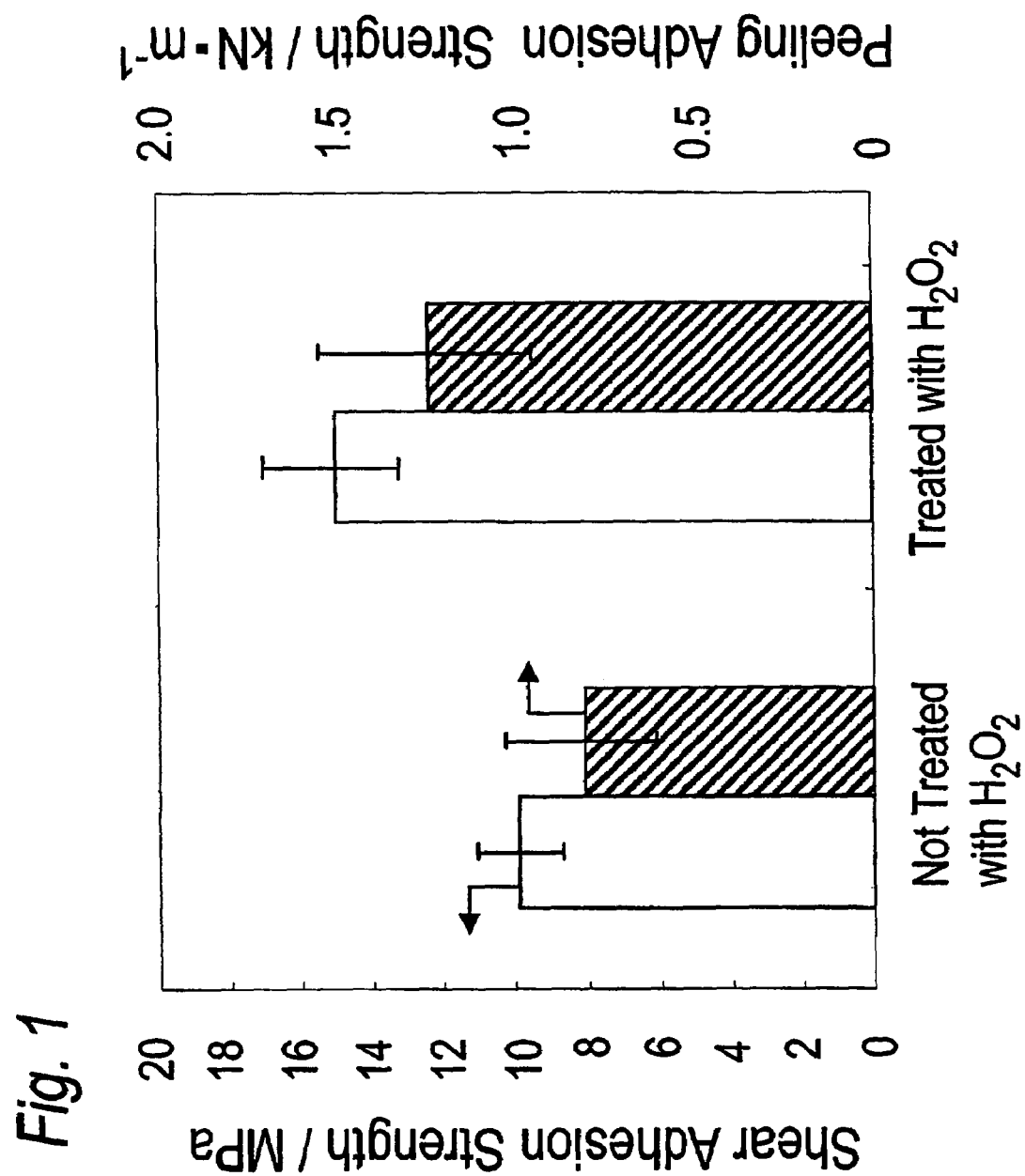
FIG. 1 is a graph showing results of adhesion test.

The substrate of the implant may be formed of various materials. For example, titanium metal and titanium alloy are preferably used because these are excellent in mechanical properties and biocompatibility. As to achieve firm attaching of the films, the substrate preferably has hydroxyl groups on its surface. Configuration of the substrate may be arbitrary selected or modified in accordance with specific uses, such as a shape of the tooth root when the implant is an artificial tooth root.

Various polymers may be used for the film; which have in its structure a functional group that itself enables adsorption of the calcium ions; or in otherwise, have a potential functional group that is to be converted to such calcium-ion-adsorbing functional group by oxidation or other treatments. When such polymers are used, it is easy to obtain the film that has, on its surface structure, the calcium-ion-adsorbing functional group. Polymers having hydroxyl groups are preferred; and, among such polymers, preferred are those which dissolve in commonly used solvents and which are easily available. Specifically, ethylene-vinyl alcohol copolymer (EVA) is preferred which easily dissolves in alcohol-water mixtures and which is commercially available as a packaging material. Polyvinyl alcohol is also preferred.

Any functional group may be adopted if and only if that is able to adsorb the calcium ion. Preferred ones are those having negative electric charge or capable to have such charge. Specifically, carboxyl group is preferred. The carboxyl group becomes anion in an aqueous solution by ionization, each to make ion bonding with two calcium ions. Meanwhile, shock-absorbing performance may be varied or adjusted by accordingly varying thickness of the film comprised of the polymer.

As for calcium phosphate forming the layer on the polymer film, hydroxyapatite is preferred because of its excellent compatibility with bones.

A method of manufacturing the implant according to the invention is as follows. On a substrate, a first film is formed which is comprised of polymer and has a functional group enabling adsorption of calcium ion. Then, the substrate having the first film is dipped in a calcium-ion solution and further in a phosphate-ion solution. In this method, the implant according to the invention is easily manufactured.

When to produce an implant that has a surface abundant of hydroxyl group, the hydroxyl group may be introduced to the implant before forming the film, by dipping the substrate in a hydrogen peroxide solution or an alkaline solution. If the substrate is formed of titanium metal or titanium alloy, the hydroxyl group may be introduced by dipping the substrate in a hydrogen peroxide solution at 60° C. for 24 hours, for example.

In order to form, on the substrate, a film abundant of a functional group that enables adsorption of the calcium ion, a film-forming material comprised of the polymer abundant of such functional group may be used as to coat the substrate. Alternatively, the substrate may be coated with a polymer without the functional group and then subjected to oxidation to form the functional group. In latter case, it is preferred that the polymer at coating has a potential functional group that is easily converted to the functional group enabling calcium ion adsorption.

As a way for forming the film of the polymer, it is easy and preferred that the polymer is dissolved in a solvent as to be applied on the substrate. Oxidation of the film of the polymer is preferably made by gas medium such as ozone gas, as to achieve a uniform oxidation irrelevant to configuration of the substrate.

When the polymer is an ethylene-vinyl alcohol copolymer, the polymer is readily dissolved in a mixture of 70-weight % of iso-propanol or n-propanol with 30-weight % of water, for example. Concentration of the copolymer in such solution is preferably in a range of 10 to 15 w/w %, in view of viscosity of the solution. After dissolving of the copolymer, the substrate is coated with the solution and then allowed to be dried. Subsequently, oxidation is made by ozone gas. In this manner, carboxyl group is introduced on surface of the film of the copolymer.

After the first film is completed on the substrate, the second film of the calcium phosphate may be formed by dipping the substrate in a calcium ion solution and subsequently in a phosphate ion solution. By this manner, enhanced adhesion strength is achieved on interfaces of the second film of the calcium phosphates. Thus formed film of the calcium phosphates is harmless for living body, and by use of the calcium phosphates, crystalline of the hydroxyapatite is easily obtained.

The dipping in the calcium ion solution and the phosphate ion solution is preferably repeated alternately. By repeating of the dipping, deposited amount of the calcium phosphate increases. Number of the alternate dipping is preferably four or more, and more preferably six or more, and still more preferably ten or more. Calcium chloride solution may be used as the calcium ion solution, and sodium dihydrogen phosphate may be used as the phosphate ion solution.

EXPERIMENT 1

Strips of pure titanium plate (JIS H 46001) having dimensions of 10 mm×50 mm×0.2 mm are provided by Fukuda Kinzoku-hakufun Kogyo, or Fukuda Metal Foil and Powder Industry. The strips are dipped in hydrogen peroxide solution of 30 wt % concentration, at 60° C. for 24 hours. Then, two of the strips are bonded together at a predetermined area by using 0.05 g of ethylene-vinyl alcohol copolymer as adhesive. Used copolymer is provided by Nippon Synthetic Chemical Industry Co. Ltd., in which a molar ratio of ethylene unit to vinyl alcohol unit is 44 mol/56 mol. For the bonding, hot pressing is made at 20 MPa for 10 minutes under temperature of 200° C. at pressing plates. The predetermined area, which is adhesion area, has dimensions of 10 mm width direction and 5 mm in length direction, of the strips. Thickness of the adhesive layer is set as 0.1 mm by interposing a 0.1 mm-thick sheet of poly-tetrafluoro-ethylene resin as a spacer between the two strips of titanium.

Mean shear adhesion strength is measured for thus obtained test pieces, by a tensile test machine ("Shimadzu Autograph DSS2000" of Shimadzu Corporation) under cross head speed of 2 mm per minute and by use of a 100 kg-scale load cell, at 25° C. The shear adhesion strength $\tau$ is expressed by a formula of $\tau=Pmax/Lb$, where "Pmax" denotes a tensile strength at breaking of the adhesive layer and "L" and "b" denotes the dimensions of the predetermined area. Further, peeling strength is measured for the obtained test pieces. For comparison, these measurements are made for test pieces obtained from the strips of titanium provided as it is without dipped in a hydrogen peroxide solution.

Adhesion strength thus measured for the strips treated with the hydrogen peroxide solution is 1.5 times of that for the strips not treated with the hydrogen peroxide solution, as the results of the measurements are shown in FIG. 1.

EXPERIMENT 2

A film of the ethylene-vinyl alcohol is subjected to ozone gas oxidation by exposing in a flow of 0.5 g of ozone per hour at 60° C., for either of 2 hours and 6 hours. Thus, carboxyl group is introduced on the surface of the film. The introduced carboxyl group is quantitatively measured by back titration using sodium hydroxide aqueous solution. Density of the carboxyl group on the film after 6 hours oxidation was higher than that after 2 hours oxidation and was determined as 0.1 $\mu mol/cm^2$.

Subsequently, the films of the ethylene-vinyl alcohol copolymer after varying oxidation are dipped in a 200 mM calcium chloride solution at 25° C. for 12 hours; where the solution is buffered with 50 mM of Tris-HCL or tris(hydroxymethyl) aminomethane-HCL as to maintain pH of 7.4. By this dipping, the calcium ions are adsorbed on the films as to be electro-statically fixed on the films of the copolymer (EVA films). Then the EVA films on the strips are dipped in a 120 mM sodium dihydrogen phosphate solution at 25° C. for 12 hours, so that calcium phosphate precipitates on surfaces of the EVA films. An X-ray diffraction measurement reveals that the precipitated calcium phosphate is in a form of crystalline of hydroxyapatite.

Dipping in the calcium chloride solution and in the sodium dihydrogen phosphate solution are alternately repeated for several times as to precipitate the hydroxyapatite crystalline in a certain thickness or in a certain density. For comparison, the EVOH films before the oxidation are directly subjected to the dipping treatment same as above.

Amounts or densities of calcium precipitation on the films are measured by use of commercially available measurement kits, in accordance with o-cresol-phthalein complexone method (OCPC method). Namely, coloring resulted from chelate bonding between o-cresol-phthalein complexone (OCPC) and calcium ion is evaluated by an absorption spectrophotometry at 570 nm. Meanwhile, amounts or densities of phosphate ion are measured by use of commercially available measurement kits, in accordance with molybdenum blue method. Namely, the phosphate is reacted with ammonium molybdate and then added with ferric ammonium sulfate; and subsequently, blue color developed by reduction reaction is evaluated by an absorption spectrophotometry at 750 nm.

Figure 2:
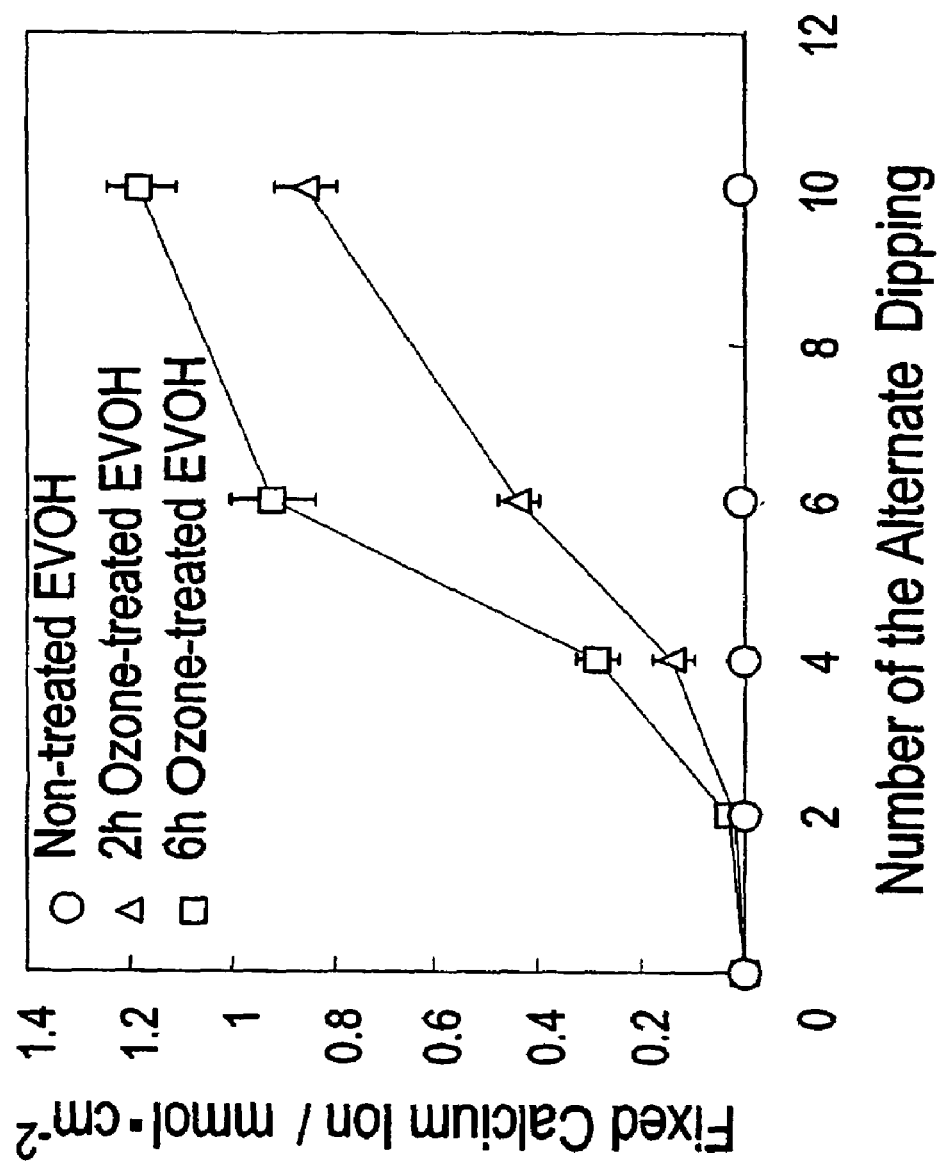
FIG. 2 is a graph showing relationship between the number of the dipping and the adsorption of calcium ion.

FIG. 2 shows relationship between number of the alternate dipping and adsorption density of calcium ion; and FIG. 3 shows relationship between number of the alternate dipping and adsorption density of phosphate. By results in the figures, it is revealed that the adsorption densities of calcium and phosphate ions are increased with increase of the number of repeated dipping. It is also revealed that precipitation density of hydroxyapatite is controlled by varying of ozone oxidation conditions or the number of repeated dipping.

EXPERIMENT 3

A substrate formed of titanium and having a configuration of tooth root is dipped in 30-weight % hydrogen peroxide solution at 60° C. for 24 hours to introduce hydroxyl group on surface of the substrates. Meanwhile, the EVOH as in Experiment 1 is dissolved in a mixture of 70-weight % of n-propanol and 30-weight % of water to give 10-weight % copolymer solution. The substrate after hydrogen peroxide treatment is coated with the copolymer solution and then dried. The substrate with thus formed films is subjected to oxidation by ozone gas flowing at rate of 0.5 g per hour, at 60° C. for 6 hours. Then, the substrate is dipped in a 200 mM calcium chloride solution having pH of 7.4 with 50 mM of Tris-HCL buffer, i.e. 50 mM of tris (hydroxymethyl) amino methane-HCL. Then, the substrate is dipped in a 120 mM sodium dihydrogen phosphate at 25° C. for 12 hours. By repeating the above alternate dipping ten times, an artificial tooth root having a hydroxyapatite layer is prepared.

Thus obtained artificial tooth root is implanted onto lower jawbone of a beagle. After three months of the implanting, a firm securing on the lower jawbone is recognized. For comparison, implanting and evaluation in the same manner is made for a conventional artificial tooth root simply made of titanium, and for an artificial tooth root having only an EVOH film on titanium substrate. By these comparative artificial tooth roots, no adhesion on the bone is recognized and the tooth roots are enclosed by fibrous tissues. Thus, invention-wise implant is superior in conglutination onto the bone.

Advantageous effect of the Invention: Invention-wise implant has a shock-absorbing property and is able to be strongly secured in a living body. And, such implant is easily obtained by the invention-wise manufacturing method.

What is claimed is:

1. A manufacturing method for an implant comprising:
    dipping a substrate in a hydrogen peroxide solution to form hydroxyl groups on a surface structure of the substrate to form a substrate having hydroxyl groups;
    forming on the substrate having hydroxyl groups a first film comprised of ethylene-vinyl alcohol copolymer having 30-50 molar % of ethylene unit, to form a coated substrate;
    introducing carboxyl groups on a surface of the first film by oxidation to form a first film having carboxyl groups; and
    subsequently, dipping the coated substrate with the first film having carboxyl groups alternately in a calcium ion solution and in a phosphate ion solution to form a second film overlaid on said first film, said second film comprising calcium phosphate.

2. The manufacturing method according to claim 1, wherein the substrate comprises titanium or titanium alloy.

3. The manufacturing method according to claim 1, wherein a density of said carboxyl group is 0.01-0.5 μmol/cm$^2$.

4. The manufacturing method according to claim 1, wherein forming said first film comprises dissolving the ethylene-vinyl alcohol copolymer in a solvent and then applying the dissolved ethylene-vinyl alcohol copolymer on the substrate having hydroxyl groups, followed by drying.

5. The manufacturing method according to claim 1, wherein the oxidation is made by ozone gas.

6. The manufacturing method according to claim 1, wherein said dipping of the coated substrate with the first film having carboxyl groups in the calcium ion solution and in the phosphate ion solution is repeated alternately six times or more in each solution.

7. The manufacturing method according to claim 1 or 6, wherein
    the calcium ion solution comprises a calcium chloride solution having a concentration of 50-500 mM and a pH of 7-8; and
    the phosphate ion solution comprises a sodium dihydrogen phosphate solution having a concentration of 50-500 mM, or a potassium dihydrogen phosphate solution having a concentration of 50-500 mM.

* * * * *